(12) United States Patent
Mah (10) Patent No.: US 6,976,013 B1
(45) Date of Patent: Dec. 13, 2005

(54) BODY SENSING SYSTEM

(75) Inventor: Robert W. Mah, Cupertino, CA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 10/874,003

(22) Filed: Jun. 16, 2004

Related U.S. Application Data (62) Division of application No. 09/652,302, filed on Aug. 28, 2000, now abandoned.

(51) Int. Cl.[7] ............................. G06E 1/00; G06F 15/18
(52) U.S. Cl. ............................. 706/27; 706/28; 706/26; 706/21
(58) Field of Search ............................. 706/27, 28, 26, 706/21

(56) References Cited

U.S. PATENT DOCUMENTS

2004/0215397 A1 * 10/2004 Cramer et al. ................ 702/19

OTHER PUBLICATIONS

The Math Works, "Neural Network Toolbox for Use with Matlab", Third Virsion, pp. 6-1 through 6-19, 1998.*

Meky et al, "Prediction of Speech Quality Using Radial Basis Functions Neural Networks", IEEE Symposium on Computers and Communications, Jul. 1997.*

Simone et al, "RBFNN-Based Hole Identification System in Conducting Plates", IEEE Transactions on Neural Networks, Nov. 2001.*

Renals et al, "A Comparative Study of Continuous Speech Recognition Using Neural Networks and Hidden Markov Models", ICASSP, Apr. 1991.*

* cited by examiner

*Primary Examiner*—George Davis (74) *Attorney, Agent, or Firm*—Robert M. Padilla; John F. Schipper (57) ABSTRACT

System and method for performing one or more relevant measurements at a target site in an animal body, using a probe. One or more of a group of selected internal measurements is performed at the target site, is optionally combined with one or more selected external measurements, and is optionally combined with one or more selected heuristic information items, in order to reduce to a relatively small number the probable medical conditions associated with the target site. One or more of the internal measurements is optionally used to navigate the probe to the target site. Neural net information processing is performed to provide a reduced set of probable medical conditions associated with the target site.

22 Claims, 6 Drawing Sheets

Tumor size is 'very large'

FIG. 4A

Tumor spiculation is 'very sharp'

FIG. 4B

Tumor 3D shape is 'moderately concave'

BODY SENSING SYSTEM

This application is a Division of an application, U.S. Ser. No. 09/652,302, filed 28 Aug. 2000, now abdn.

ORIGIN OF THE INVENTION

The invention disclosed herein was made by employees of the United States Government and may be manufactured and used by or for the Government for governmental purposes without payment of any royalties for such manufacture and use.

FIELD OF THE INVENTION

This invention relates to navigation to, and imaging, sensing, diagnosing, and providing a prognosis for a medical condition of, a target site within a human or animal body.

BACKGROUND OF THE INVENTION

Use of a conventional surgical procedure to provide a diagnosis and/or prognosis on a patient is necessarily invasive. Where a surgical probe is used to reduce the invasiveness, the procedure is often performed blindly or with indirect image guidance, with little accurate information on the location of the probe and/or whether the probe has located, navigated to or reached the target site. One result of a conventional approach is an increased number of false positive test results and false negative test results that directly affect the diagnostic results and the results of subsequent surgery at the target site. For example, about 37 percent of patients undergoing epidural anesthesia require three or more attempts at epidural placement. In another direction, about 20 percent of instances of prostate cancer are missed (false negative test result) by performance of a blind biopsy.

What is needed is a system and associated method that allows navigation to a target site and uses results from several different tests to identify a malignancy, a disease, a benign condition, a normal condition or any other medical condition (collectively referred to as "medical conditions" herein) at the target site from a reduced group of such conditions that may be present, consistent with the data obtained from various measurements and other information. Preferably, the system should work with quantitative measurements, with qualitative measurements and with other relevant information on the subject and the subject's family. Preferably, the system should allow inclusion or exclusion of one or more selected measurements and information items without reconfiguration of the analysis of the data presented and should allow assignment of selected weights to different data items, corresponding to the importance of a data item in identifying presence of a particular medical condition.

SUMMARY OF THE INVENTION

These needs are met by the invention, which provides an active system for measuring and determining the location, geometric parameters and medical condition(s) of a target site (organelle, cell, tissue, organ, etc.) within the body of an animal or a human being (collectively referred to herein as "animal"). The system relies upon measurements and other information from one or more of at least three types of sources: external measurements, from sources such as lymph node sampling, manual palpation of the target site, mammograms, ultrasound scans, NMRI scans, CAT scans, estimation of target site size, surface roughness and/or calcification at the site and other similar functionalities; internal sensor measurements, including mechanical stiffness, thermal responsiveness, optical reflectance and imagery, target margin behavior, blood flow estimation, interstitial fluid pressure, vascular size, density and architecture, pH and electrical characteristics; and heuristic information involving prior medical history of the test subject and the subject's family.

Most or all of the measurements and information items are used to estimate the present location, present size and other geometric parameters, present medical condition and/or prognosis of the target site, by excluding or ruling out certain location and/or geometric parameters and/or other medical conditions. No one test determines the results. Most or all of the measurements are used in combination to estimate the present medical condition of the target site.

Each internal measurement, external measurement and heuristic information item that lies in a selected range indicates possible presence of a group of medical conditions that is wholly, or largely, consistent with these data. In one approach, the set intersection of these different groups may be formed to provide a reduced group of medical conditions that is wholly, or largely, consistent with these measurements and information items.

DESCRIPTION OF BEST MODES OF THE INVENTION

Figure 1:
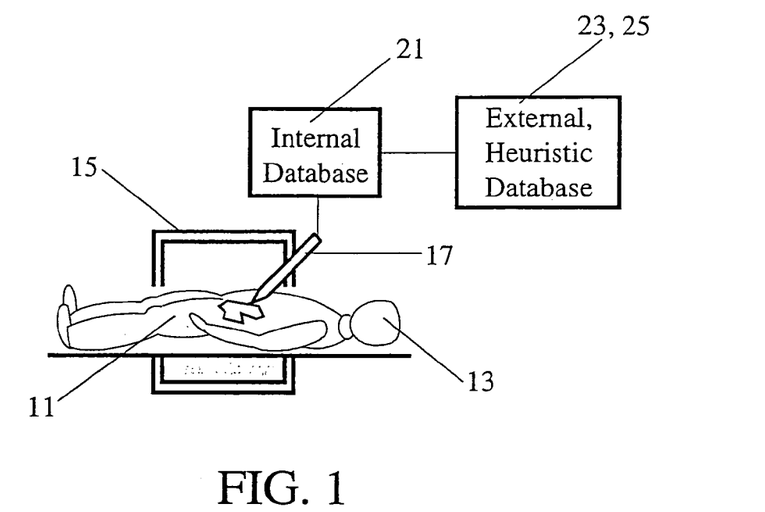
FIG. 1 is a schematic view of use of the system to sense a target site in a human's body according to the invention.

FIG. 1 illustrates use of the invention to interrogate a target site 11 (organelle, cell, tissue, organ, etc.) in an animal body 13 according to one embodiment of the invention. A sensor or probe is inserted into the body 13 adjacent to the target site 11 and is activated to provide one or more internal measurements, which set forth in more detail in FIG. 2. A region of the body 13 adjacent to the target site is immobilized (to the extent this is possible) by a stereotactic or other body-holding device 15, and a sensor assembly or probe 17 is positioned adjacent to or within the target site, outside or inside the body. Internal measurements data are sensed or measured by the probe 17 and are received and stored by an internal data base 21. An internal data base 22, an external data base 23 and a heuristic database 25 hold internal measurements data external measurements data and heuristic information, respectively, also set forth in greater detail in FIG. 2.

Figure 2:
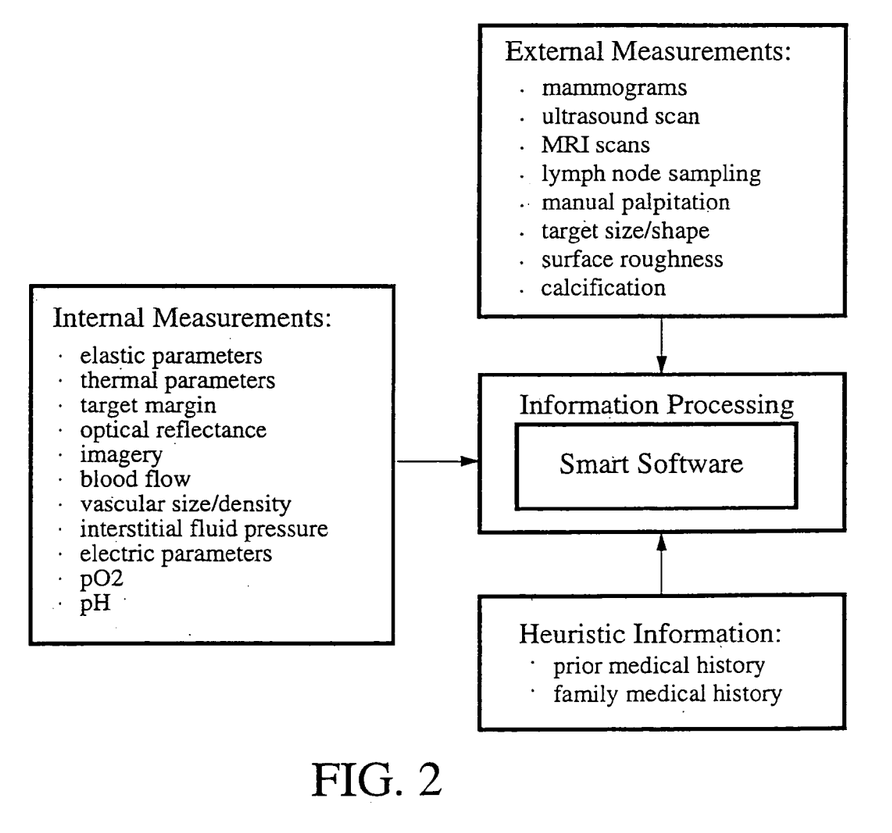
FIG. 2 illustrates, in block diagram format, some of the four types of measurements used in practicing the invention.

FIG. 2 sets forth three kinds of data that are used to help determine one or more medical conditions of the target site 13: internal measurement sets, external measurements and heuristic information. Internal measurements include: (1) elasticity parameters of the target site and surroundings; (2) thermal parameters of the target site and surroundings; (3) optical reflectance of selected portions of, or all of, the target site surface and/or interior; (4) target margin characteristics for the target site; (5) estimates of blood flow within and/or adjacent to the target site; (6) vascular size, density and/pr architecture within and/or adjacent to the target site; (7) interstitial fluid pressure within and/or adjacent to the target site; (8) oxygen tension pO2 in a selected region within and/or adjacent to the target site; (9) pH of a selected region within and/or adjacent to the target site; (10) electrical parameters of a selected region within and/or adjacent to the target site; and (11) other relevant parameters.

Elasticity parameters include Young's modulus (resistance to strain imposed in a first direction when the body is unconstrained in any transverse direction), bulk modulus (resistance to change of three-dimensional volume), Poisson's ratio (change in dimension in a first direction in response to an imposed change in dimension in a second direction), and other similar parameters. One or more of the elastic parameters can be determined by observing a target site response to an abrupt step function force, to a slowly applied mechanical force and/or to a time varying force (such as a sinusoidal force). For example, presence of a tumor at a target site may increase the Young's modulus by 400–900 percent, relative to the Young's modulus of a normal or healthy target site. No single parameter obtained from internal measurements is sufficiently specific that measurement and comparison of these parameter values with corresponding values for a "normal" target site will determine, by themselves, the nature of the abnormality present. Thermal parameters include local temperature, thermal conductivity and specific heat capacity of a selected region adjacent to or within the target site. Specific heat capacity of a normal organ or tissue, for example, has an estimated range of about $c_p$=0.9–1 cal/gm/° C., whereas an organ or tissue that includes a tumor may have a higher range for $c_p$ (reflecting the more "solid" nature of a tumor) or may have a lower range for $c_p$ (reflecting the interrupted and irregular nature of blood flow, and thus temperature regulation, within a tumor). The temperature of a normal organ or tissue within a human may have a range T= 37–38° C., whereas the temperature of an organ or tissue with certain diseases present may have a range several degrees Celsius higher.

Optical reflectance of a selected portion of, or all of, a target site is best evaluated by dividing a selected region of wavelengths $\lambda$, for example, 200 nm $\leq \lambda \leq$ 1200 nm, into wavelength bins of selected length $\Delta\lambda$, where $\Delta\lambda$ may be 10 nm–100 nm, depending upon the medical condition being assessed. Optical reflectance OR($\lambda$;meas), measured for the target site, is compared with "normal" optical reflectance OR($\lambda$;normal) for each of a selected sequence of wavelength ranges to estimate whether the target site is abnormal, and if so, what is the group of medical conditions that presently affect the target site.

J. Mourant et al, in "Spectroscopic Diagnosis of Bladder Cancer With Elastic Light Scattering, Lasers in Surgery and Medicine, vol. 17 (1995) pp. 350–357, have examined ten patients with suspected bladder cancer, using one or more optical fibers to illuminate a region and another optical fiber to collect the backscattered light in a wavelength range 250 nm $\leq \lambda \leq$ 900 nm. These optical biopsy results were compared with actual biopsies performed at the same sites. After subtracting a dark background that is common to all measurements at each of a sequence of wavelengths, these workers found that for 20 malignant regions, the normalized optical reflectance spectrum had a strong negative slope in the wavelength region 330 nm $\leq \lambda \leq$ 370, while 29 of 30 non-malignant regions had a normalized optical reflectance spectrum with a modest positive slope for the same wavelength region; the specificity for this test, based on the ten patients examined, is 97 percent.

Use of optical reflectance to serve as a guide in navigating a probe within brain tissue, and distinguishing white matter from gray matter therein, is reported by H. Liu et al in "Investigation of Optical Reflectance from Human Brain in vivo for Guiding Brain Surgery" [citation]. White matter reflectance is 3–5 times as large as gray matter reflectance in a wavelength region 600 nm $\leq \lambda \leq$ 800 nm, and this difference appears to extend to higher and lower wavelengths as well. A transition region near the gray-white matter boundary witin a brain has optical reflectances that are intermediate between the gray matter and white matter values.

The margins of certain tumors may have certain characteristics that differ from the corresponding characteristics for the core or interior of the tumor. For example, the increased interstitial fluid pressure in the core of a tumor drops sharply to that of a normal region near an edge of a tumor, as reported by P. Vaupel, in "Vascularization, blood flow, oxygenation, tissue pH, and bioenergetic status of human breast cancer", *Oxygen Transport to Tissue*, Plenum Press, New York, vol. 18 (1997), pp. 143–154, and discussed in greater detail in the following. Comparison of these characteristics for the margin(s) and for the core, using selected scanning or imaging techniques, may help distinguish between the presence and absence of certain kinds of tumors. The size of a margin or transition region may also indicate presence of a non-normal target site. For example, a margin size for a well developed tumor is typically about 2.7 mm.

An estimate can be made of blood flow velocity adjacent to or within the target site using a sensor that estimates blood flow using a Doppler velocity sensor or similar indirect estimating procedures. For a normal breast, a breast with a benign tumor and a breast with a malignant tumor, measured mean blood flow values are 311±157 flux units, 482±209 flux units and 711±280 flux units, respectively. Thus, larger than normal blood flow velocity appears to indicate presence of a benign or malignant tumor.

Where measured vascular density for a target site is higher, by a multiplicative factor of 2–10 or higher, than a normal range of vascular density (e.g., 2–3 per mm$^2$) for that site, this condition often indicates the presence of a malignant tumor. Comparison of measured vascular size with vascular size range for a normal target site (e.g., 0.2 mm) can indicate presence of a class of non-normal medical conditions (benign or malignant), especially if the measured size is at least 200 percent higher than the normal range of sizes.

P. Vaupel, op cit, notes that growth of an avascular, three-dimensional aggregate of tumor cells is self-limiting. The establishment of progressive expansion of malignant tumors is possible only if supply and drainage are initiated through blood flow through exchange vessels in a tumor bed, using pre-existing normal host blood vessels and using newly-formed tumor vessels arising from neovascularization. Angiogenesis, the formation of new capillaries from an existing vascular network, appears to be essential for tumor growth and metastasis, and some angiogenesis parameters (pO2, vascular count, vessel morphology, etc.) can also be used for prognosis. Greater vascular density may be associated with longer patient survival, although some other studies reach an opposite conclusion. A growing tumor is unable to form its own lymphatic system and must rely on other sources for blood, nutrients, oxygen, etc. Bulk flow of free fluid in interstitial spaces appears to be much higher in a tumorous region than in a normal region: 15 percent of normal convective plasma flow for breast cancer regions versus 0.5–1 percent of normal convective plasma flow for a normal region. These increased interstitial fluid pressures drop sharply near the edge of a tumor.

Interstitial fluid pressure (IFP) is a measure of a balance of fluid entering a target site and fluid exiting from the target site. Only an invasive breast tumor has a consistently higher IFP value (15–32 mm Hg) than does a normal or healthy breast (−0.4 to +4 mm Hg), where an IFP measurement needle tip is located within the tumor region. The results reported in the preceding paragraph by Vaupel, op cit, are also relevant here.

Comparison of oxygen tension pO2 (or PPO) for a selected region adjacent to or within the target site with corresponding values for a normal target site can provide an indication of whether or not a particular class of medical conditions is present. Vaupel, Kallinowski and Okunieff, in "Blood Flow, Oxygen and Nutrient Supply, and Metabolic Microenvironment of Human Tumors; A Review", [citation] report on a study of change of pO2 in cervical mucosa with progress of cervical cancer. In a normal, non-cancerous cervix, the the pO2 median value is 36 mm Hg. For stages 0, 1 and 2 of cervical cancer, the pO2 median value drops to 20 mm Hg, to 13 mm Hg and to 5 mm Hg, respectively. The measured pO2 value appears to move to lower and lower values as cancer progresses, as compared to a normal or healthy range for the cervix. A non-metastasising breast tumor (pO2≈20 mm Hg) has a larger mean pO2 value than does a metastasising breast tumor (pO2≈7.5 mm Hg). Based on other measurements reported, a tumor growing in association with an organ appears to require at least 50 percent more oxygen than a normal organ, and this may be manifested by a much smaller pO2 value where a tumor is present.

Results reported by Vaupel, op cit, on oxygen consumption in a breast cancer tumor (3–10 $\mu$l/gm/min) versus oxygen consumption in a normal region (3–6 $\mu$l/gm/min) are consistent with these results. Hypoxia is present in many tumorous regions. Vaupel found pO2 values of 0–2.5 mm Hg for breast tumors and pO2 values of at least 12.5 mm Hg for normal regions. A bimodal pO2 distribution is often manifested, indicating presence of normal and hypoxic regions side by side.

The pH of a selected region adjacent to or within a target site can be measured and compared with a normal range of pH for the target site, as an indicator of the possible presence of one or more of a class of medical conditions. A normal target site will have a steady state pH of 7–7.4, reflecting the corresponding values of blood pH. Extracellular pH has a mean value of 7.35 for a normal target site and 7.0 for a tumorous target site. Intracellular pH has a mean value of 7.04 for a normal target site and 7.2 for a tumorous target site. For a tumorous cell, pH(intracellular) is significantly greater than pH(extracellular). However, mislocation of the site of measurement of pH (inside versus outside a cell) may lead to a wrong conclusion concerning the condition of the cell or target site.

Vaupel, op cit, reports that the intracellular pH is neutral to mildly alkaline for tumorous cells that are not deprived of oxygen or energy, while the extracellular pH is acidic. This cross-membrane gradient for a tumorous cell is opposite in sign to the cross-membrane gradient for a normal cell, where pH(intracellular) is lower than pH(extracellular).

A. J. Surowiec et al, in I.E.E.E. Trans. on Biomedical Engineering, vol. 35 (1988) pp. 257–262, report on measurements of dielectric parameters at frequencies up to 100 MHz. These workers find that electrical conductivity in tumorous breast tissue is 100–200 percent higher than electrical conductivity in normal breast tissue: 2–3 mS/cm versus about 1 mS/cm. Other tissues are believed to be similarly affected by changes in structure and composition, due to cell proliferation and tumor growth, and similar differences in electrical conductivity and other dielectric parameters is expected for other tissues.

The sensor assembly and probe 17 can also be used to assist the probe in navigating to the target site, preferably in real time. One approach here uses general shapes, assumed to be known, and imaging of the organs and major tissue groups to move the probe to a location adjacent to the target site. At this location, the probe can perform certain internal measurements outside the target site, before the probe is moved within the probe site for additional measurements.

Data from external measurements, not relying upon measurements taken with the sensor assembly and probe 17, may also help limit the class of medical conditions, if any, present at the target site. One example is data extracted from mammogram imaging performed on an adult female. This image may: (1) indicate the likely presence of a particular disease (e.g., cancer of the breast); (2) be consistent with, but not unambiguously indicate the presence of, a particular disease; or (3) may be inconsistent with, or be contraindicative of, the presence of a particular disease. Another example is a protein specific antigen (PSA) test, performed on an adult male, to detect the (increasing) likelihood of presence of prostate cancer.

Another class of external measurements are the NMRI scans, CAT scans, ultrasound scans and mammograms, which provide data on or adjacent to a target site that can be compared with data from measurements on normal target sites.

Another class of external measurements are lymph node samples, which may indicate presence of a normal medical condition or of a precursor or a vestige of a non-normal medical condition, such as HIV, that is not yet present, or is no longer present, at other sites within a body.

Another class of external measurements involve simple manual palpitation of a region of a body and comparison of the response with an expected response from a normal, undiseased body.

The size and/or shape of a target site can be estimated, using scanning or imaging (NMRI or ultrasound), or using a sequence of two or more measurements, taken at different locations relative to the target site, and some analytical geometry computations to estimate the parameters of an ellipse that approximately coincides with the target site, as discussed in the following.

The roughness (spiculation) of a target site surface can be estimated using an NMRI scan or ultrasound scan. Spiculation associated with a boundary of a tumorous target site may differ significantly from spiculation of an adjacent normal site. This difference should be evident from the results of an NMRI scan or ultrasound scan, if the region interrogated can be made smaller than the present size of a tumor.

A measurement or other estimate of the amount of calcification associated with a target site can be estimated, using optical imaging, NMRI scanning, ultrasound scanning or (preferably) a mammogram, and can be compared with the amount and pattern of calcification associated with a normal or benign target site to determine whether a class of medical conditions is likely to be present.

Size, surface roughness and calcification associated with a target site are (somewhat arbitrarily) treated as external measurements because these parameters are often obtained using NMRI and/or ultrasound scanning to provide the data. However, one or more of these information items could also be treated as an internal measurement.

Heuristic information, including but not limited to medical history of the subject and of the subject's family, may be used to provide an indicator of consistency or inconsistency of an extant prognosis determined from internal and/or external measurements. For example, the subject's family may have an extensive medical history of cancer involving a particular group of organs (e.g., breast, prostate and colon), which should be taken into account in any diagnosis or prognosis at a target site.

The external measurements and the heuristic information provide data that are often not directly and numerically comparable with corresponding data for a normal target site. The external measurements data and/or heuristic information are preferably analyzed using a fuzzy logic interface that does not rely upon comparison of numerical values but that can return a (fuzzy) determination that it is more likely that not that a particular medical condition is, or is not, present. For example, comparison of a calcification pattern for an observed target site with a calcification pattern for a corresponding normal target site may be performed visually and subjectively by a health care professional and/or may be performed by a software algorithm, relying upon fuzzy logic and the nature of the pattern differences rather than upon a hard-edged comparison of one or more numerical parameters for the patterns. Fuzzy logic is discussed by B. Kosko and S. Isaka in "Fuzzy Logic", Scientific American, July 1993, pp. 78–81.

Data from any of the preceding N1=10 groups of internal measurements, from the N2=7 groups of external measurements and/or from the N3=2 groups of heuristic information are preferably analyzed using a direct interface with analytical software that is part of the system. Some of these numerical data may be directly compared with corresponding numerical ranges to determine whether a particular medical condition is likely to be present at the target site. Each group of internal measurement data, each group of external measurement data and each group of heuristic information items provides a more or less independent dimension in a "medical condition space" of dimension N1+N2+N3. Preferably, each medical condition that is present in, or is wholly or largely consistent with, the measurements in each of these dimensions has an associated confidence level, with values ranging from 0 percent to 100 percent.

Figure 3:
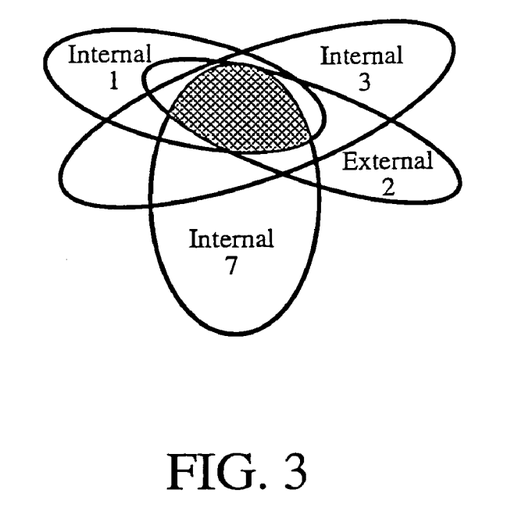
FIG. 3 graphically illustrates formation of a set intersection of groups of possible medical conditions according to the invention.

Presence of a medical condition, especially a non-normal one, in each of two or more such dimensions affirmatively indicates the possible presence of that medical condition, as discussed in the preceding. When this occurs, an initial diagnosis uses the set intersection of the medical conditions in each dimension to provide a list of medical conditions that is consistent with the medical conditions present in each dimension. FIG. 3 graphically illustrates provision of a reduced group of medical conditions from intersection of groups numbered 1, 3 and 7 of the internal measurement data and group number 2 of the external measurement data, as an example.

Internal measurement data, external measurement data and heuristic information are preferably analyzed using a neural network that is configured as discussed in the following.

Figure 4A:
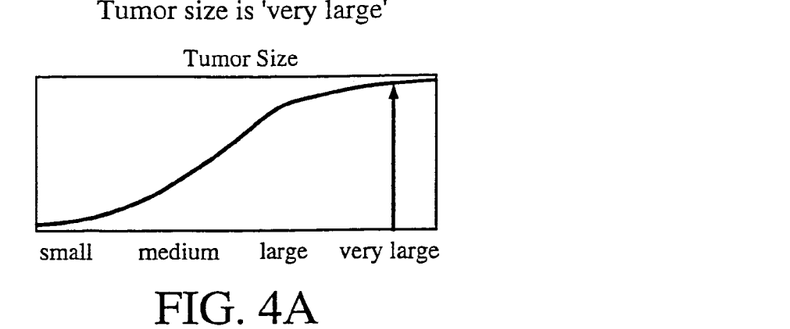
FIGS. 4A–4D graphically illustrate data and a result of analysis of these data according to the invention.
Figure 4B:
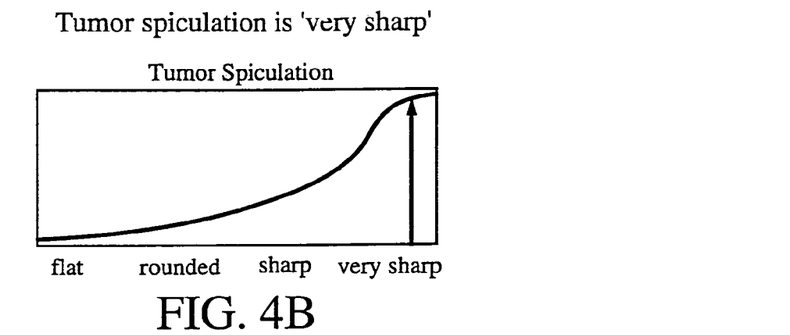
Figure 4C:
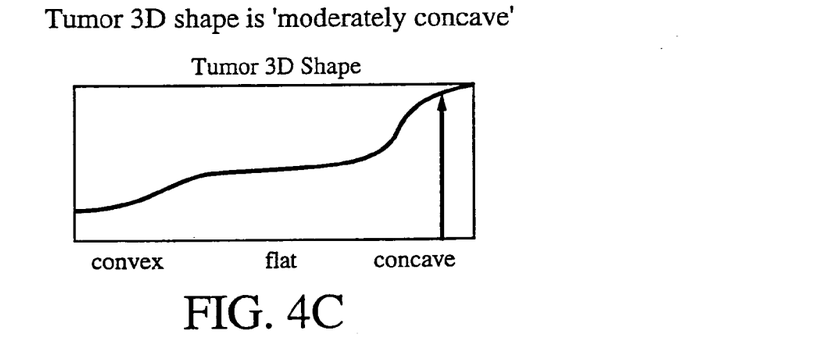
Figure 4D:
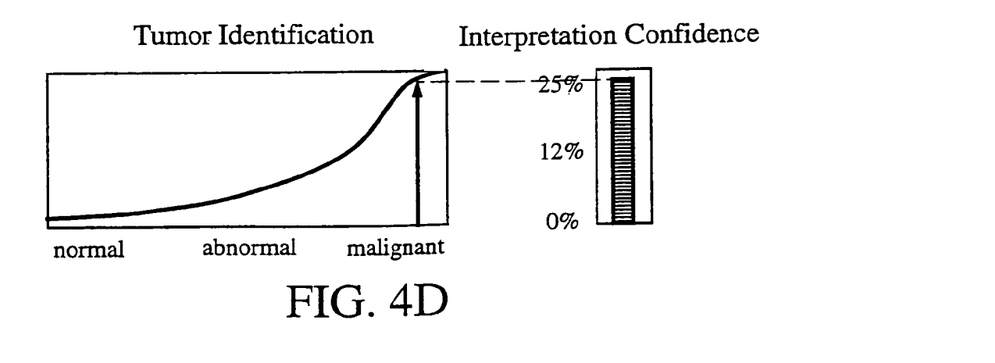

FIGS. 4A, 4B and 4C graphically illustrate certain quantitative external measurement data that might be obtained for a target site at which a tumor may be present, indicating target site size (FIG. 4A), spiculation (FIG. 4B) and shape (FIG. 4C). FIG. 4D indicates a possible result of analysis of the results obtained from the data shown in FIGS. 4A, 4B and 4C. In this instance, the confidence level that the target site includes a malignant tumor is about 25 percent, which may be large enough to warrant performance of more invasive exploratory and corrective surgery.

Figure 5:
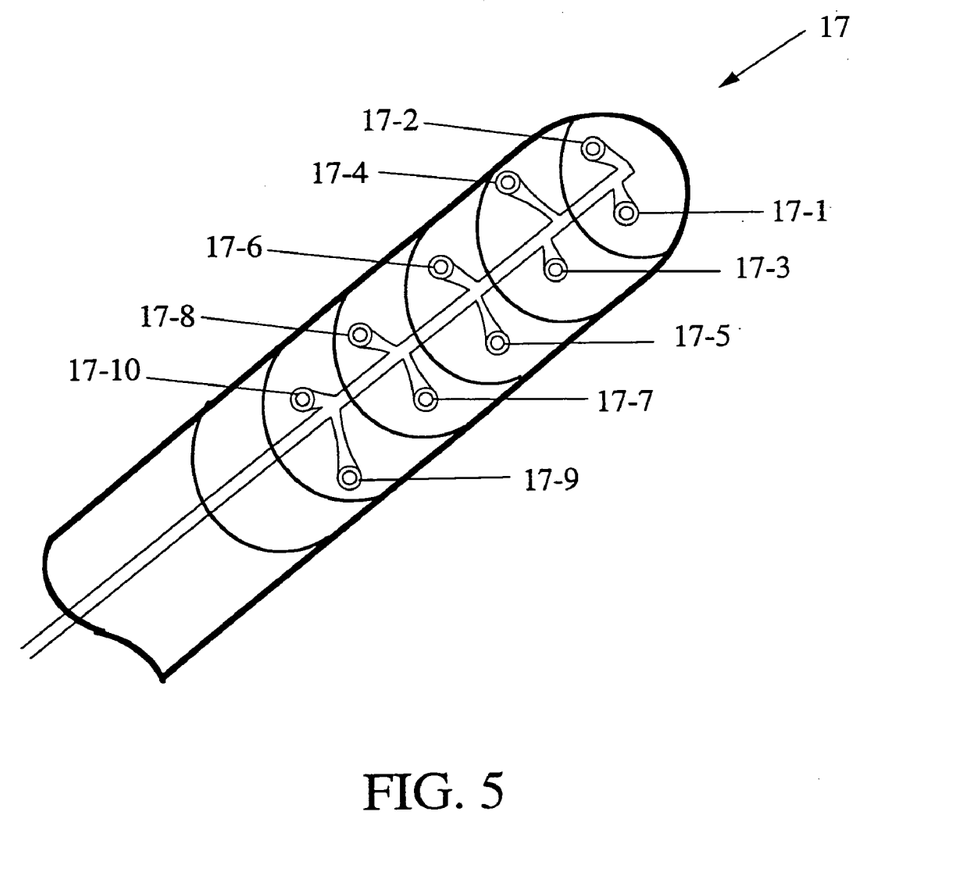
FIG. 5 is a schematic view of a probe constructed according to the invention.

FIG. 5 is a schematic view of a sensor assembly and probe 17 including mechanisms to perform measurements associated with each of the ten types of internal measurements discussed in the preceding. A first probe mechanism 17-1 measures one or more elastic parameters associated with the target site, preferably including at least one of Young's modulus and bulk modulus. A second probe mechanism 17-2 measures one or more thermal parameters, drawn from a group consisting of local temperature and specific heat capacity associated with the target site. A third probe mechanism 17-3 measures optical reflectance $OR(\lambda;meas)$ of a selected region of the target site for one or more selected wavelength ranges. A fourth probe mechanism 17-4 measures one or more characteristics of the margin of a target site. A fifth probe mechanism 17-5 measures amount of blood flow adjacent to or within the target site. A sixth probe mechanism 17-6 measures vascular size and/or vascular density associated with the target site. A seventh probe mechanism 17-7 measures interstitial fluid pressure associated with the target site. An eighth probe mechanism 17-8 measures oxygen tension $pO2$ associated with the target site. A ninth probe mechanism 17-9 measures local pH associated with a selected portion of the target site. A tenth probe mechanism 17-10 measures one or more electrical parameters associated with a selected portion of the target site. One or more of these probe mechanisms can be included in the probe; and one or more of these probe mechanisms can be included in each of two probes that cooperate to sense and measure various internal data for comparison. Optionally, the probe 17 may also be configured to measure one or more parameters associated with size, shape, surface roughness and/or calcification pattern associated with a target site.

Figure 6:
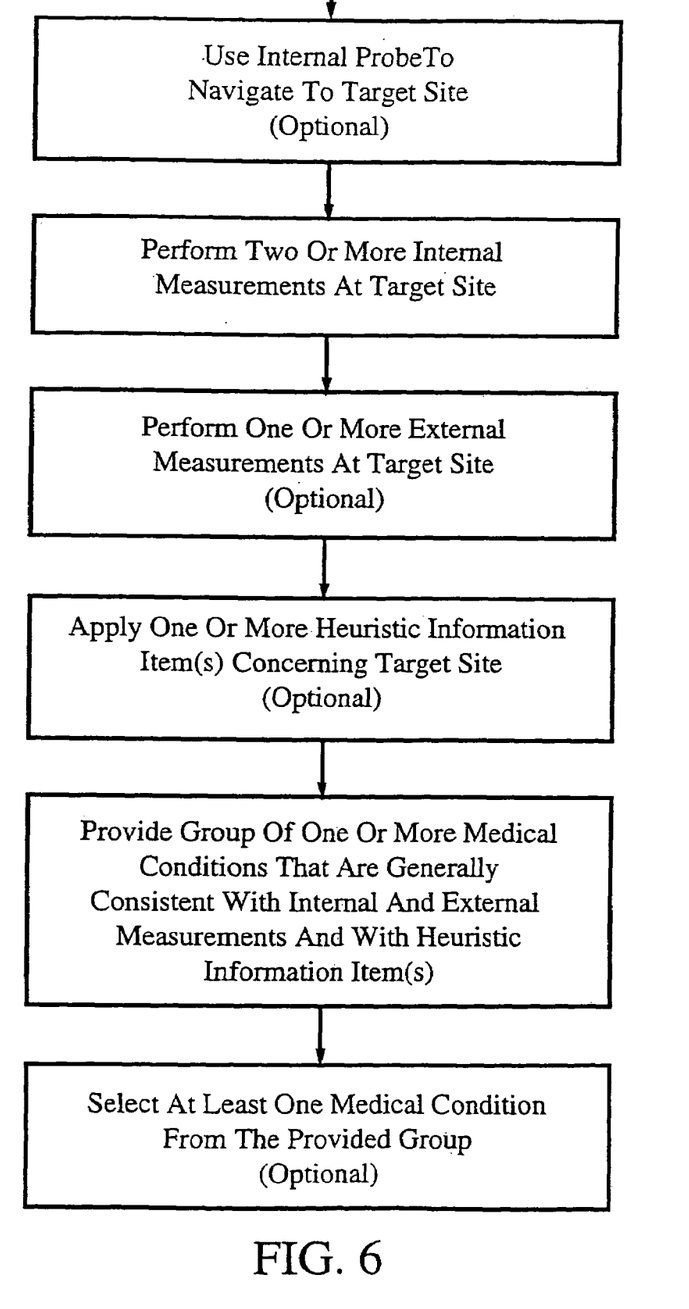
FIG. 6 is a flow chart of a procedure to practice the invention.

FIG. 6 is a flow chart of a procedure for practicing the invention. In step 61 (optional), an internal probe is used to aid in navigation of the probe to a target site (e.g., using optical reflectance of organs and/or tissues along a path to the target site), with appropriate confidence levels incorporated. In step 63, two or more internal measurements are performed at the target site using the probe, with appropriate confidence levels incorporated. In step 65 (optional), one or more external measurements are performed at the target site, with appropriate confidence levels incorporated. In step 67 (optional), one or more heuristic information items concerning the target site are included, with appropriate confidence levels incorporated. In step 69, a group of one or more medical conditions, each of which is generally consistent with the internal measurements, with the (optional) external measurements, and with the (optional) heuristic information items, is provided. In some instances, an internal measurement, an external measurement and/or a heuristic information item that is inconsistent with the remainder of the data for the target site may be either ignored or given much smaller weight, or even negative weight, in determining this group of medical conditions. In step 71, at least one medical condition from the provided group is identified as likely to be present for the test subject.

One approach to processing and analyzing the results of comparison of one or more internal measurements at a target site with selected reference values corresponding to a normal or benign medical condition, or corresponding to a malignant (tumorous) medical condition, is through neural net processing. At least two alternatives are available: radial basis neural net modeling and backpropagation modeling.

Figure 7:
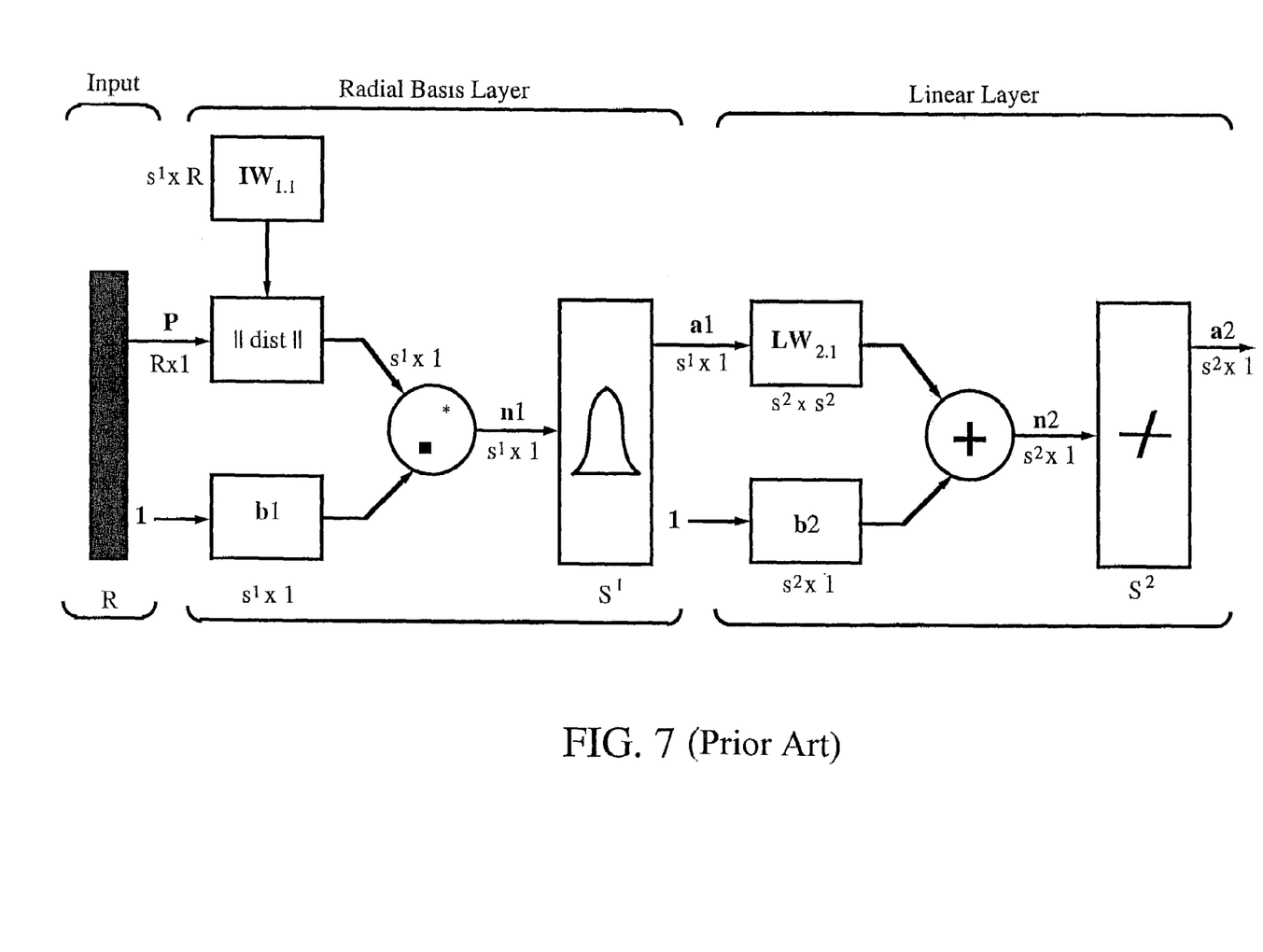
FIG. 7 is a schematic view of one approach to neural network modeling and processing of information provided by the invention.

Radial basis neural net modeling ("NNM") is summarized in *Neural Network Toolbox For Use With Matlab*, The Math Works, Third Version, 1998, pp. 6–1 through 6–19, and is characterized in FIG. 7. This neural network includes three layers, an input layer 81, one or more hidden layers 83, and an output layer 85. The input layer 81 accepts an input vector p, forms a difference between the vector p and an input weight vector w, optionally multiplies the difference p−w by a selected bias or sensitivity vector b to form a scalar product, and passes this scalar product to an intermediate layer for further processing and analysis.

The dimension N of the vectors p and w may be the total number of independent internal measurements plus independent external measurements plus heuristic information items presented for the test subject. For example, if three internal measurement sets (1, 3, 7), one external measurement set (4) and one heuristic information item (1) are presented, as in FIG. 3, the dimension N= 3+1+1=5. More likely, the dimension N will be a larger number, in order to obtain discrimination between two medical conditions having similar data for "lower dimensional" measurements.

The radial basis neural network ("RBNN"), shown schematically in FIG. 7, will produce an output value OUT that is close to zero, if the vectors p and w differ substantially from each other and will produce an output value OUT≈1 if the vectors p and w are (nearly) equal to each other. One object of processing by an RBNN is to identify an input vector p that provides an output value that is close to, or equal to, 1 for one or more of a selected sequence of input weight vectors w. In this RBNN analysis, more than one input weight vector w may be used at the same time.

Consider an R-dimensional space S having a finite collection of Q reference data points therein, each with coordinates $x(q)=(xq1, xq2, \ldots, xqR)$ ($q=1, 2, \ldots, Q$), with each point in this collection representing a reference data point with an associated medical condition for a selected target site. The data represented by the point x(q) are taken from certified observations made on one or more reference test subjects and include data from internal measurements, from external measurements and from heuristic information on medical condition of the target site. Preferably, each R-dimensional space S is associated with a different target site (brain, heart, liver, pancreas, kidney(s), intestines, lung(s), thorax, selected tissues, selected groups of cells associated with a given organ, etc.) for the reference test subjects. Each reference data point x is associated with one of K=2 medical conditions for the target site: malignant (M) or normal/ benign (B). More generally, each reference data point x is associated with one of K ($\geq 2$) selected medical conditions for the target site.

Assume that a patient (a non-reference test subject) is subjected to probing with the probe and/or scanning according to the invention for a selected target site and that internal and/or external measurements produce at least one observed data point $y=(y1, y2, \ldots, yR)$ in the space S. The distances $\{d(x(q);y)\}$ ($q=1, 2, \ldots, Q$) are compared with each other, and at least one reference data point x(q0) satisfies $$d(x(q0);y)=\min_q\{d(x(q);y)\}. \quad (1)$$

The distance d(x(q);y) may be defined generally as $$d(x(q); y) = \left\{\sum_{r=1}^{R} w_r |xqr - yr|^s\right\}^{1/s}, \quad (2)$$

where $w_r$ is a selected non-negative weight value and s is a selected positive number. The choice $\{w_r=1, s=2\}$ recovers the conventional Euclidean distance metric. A more general distance metric d(x(q);y) may also be used here that satisfies three standard requirements for a metric: (1) $d(x,y) \geq 0$, (2) $d(x,y)= d(y,x)$ and (3) $d(x,z)+d(z,y) \geq d(x,y)$.

Assume, for definiteness, that a reference data point x(M1), belonging to the malignant set M, is found to be closest to the observed data point y so that x(q0)=x(M1) satisfies the relation (1). For illustrative purposes, the two next-nearest reference data points are assumed to be x(B1) and x(B2), belonging to the normal/benign set (referred to collectively as the "normal" set) B. For purposes of initial illustration, the dimension of the space S is assumed to be R=1 in FIG. 8A so that the space is a line segment, having a single coordinate y, with each reference data point having a location on that line segment.

Observed data points y that are "close to" a reference data point, such as x(M1), on this line segment will have a correspondingly high overall probability Pr[y] that the medical condition of the target site belongs to the malignant set M. Observed data poiints on this line segment that are "close to" a reference data point, such as x(B1) or x(B2), on this line segment will have a correspondingly high overall probability that the medical condition of the target site belongs to the normal set B. A probability function $$Pr(x(q);y)=F(d(x(q);y);q) \quad (3)$$

is assigned to each of the Q reference data points, where F is a monotonically decreasing (preferably continuous) function of the distance d(x(q);y) between the observed data point y and the reference data point x(q). Each function F satisfies $0 \leq F \leq 1$ and may vary with the index q as well. In one version of the first and second embodiments, the probability function F(d(x(q);y);q) is the same for all reference data points x(q) belonging to a malignant medical condition set (M) and is the same for all reference data points x(q) belonging to a normal medical condition set (B). Use of a probability function F that varies more generally with the index q complicates the analysis but can be incorporated. Suitable classes of probability functions F include exponential $$F(d(x;y))=\exp\{-\alpha \cdot d(x;y)^p\}, \quad (4A)$$

inverse polynomial $$F(d(x;y))=\alpha/\{\beta+\chi \cdot d(x;y)^p\}, \quad (4B)$$

and linear or nonlinear $$F(d(x;y))=\alpha-\beta \cdot \{d(x;y)^p\}, \quad (4C)$$

where $\alpha$, $\beta$, $\chi$ and p are selected real numbers.

Figure 8A:
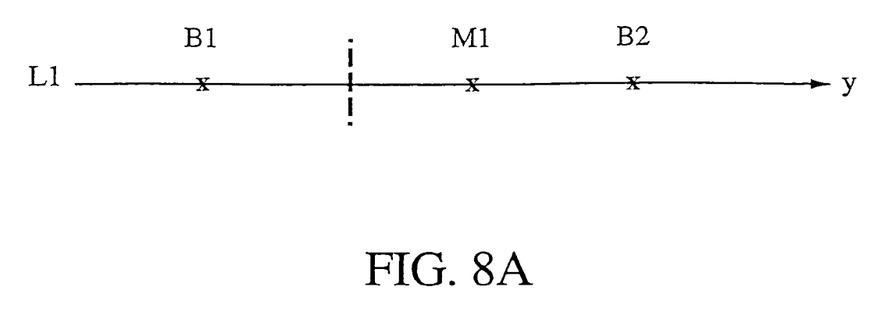
FIGS. 8A and 8B are one-dimensional illustrations of a comparison of reference data points and observed data points according to the invention.
Figure 8B:
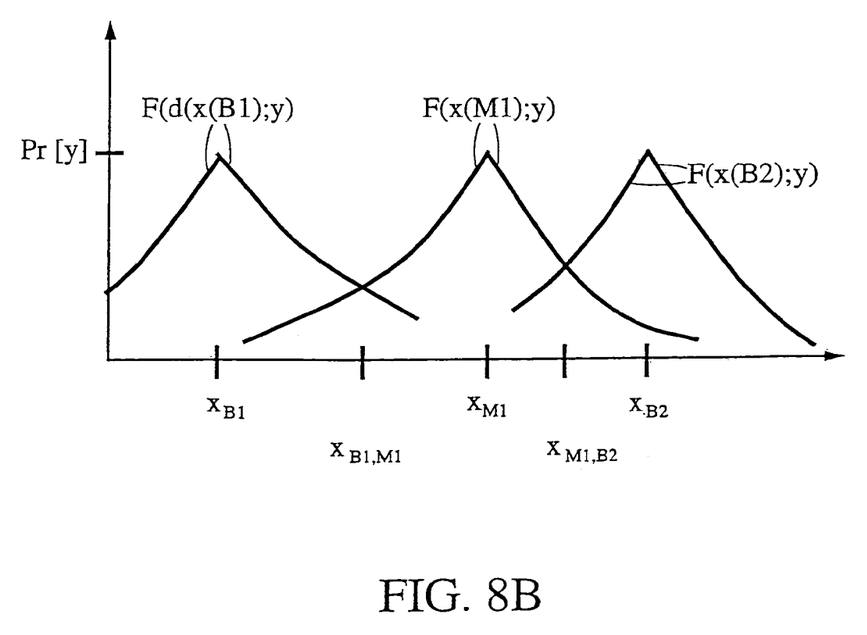

If the reference data point x(q) corresponds to a malignant medical condition (or to a normal medical condition), F(d (x(q);y);q) corresponds to a probability that the observed data point is indicative that the observed data point belongs to the set M (or to the set B). FIG. 8B graphically illustrates, in one dimension, three typical probability functions for the reference data points B1, M1 and B2. Note that, for example, the probability functions corresponding to B1, to B2 and to M1 need not be the same. The one-dimensional situations illustrated in FIGS. 8A and 8B are easily generalized to R dimensions, using the distance metric d(x(q);y). The relative positions of the data points B1, B2 and M1 may be changed as long as at least one normal data point (B1 or B2) and at least one malignant data point (M1) are present.

In one embodiment, the overall probability associated with the target site (represented by the observed data point y) is $$Pr[y] = \max_q F(d(x(q);y);q), \quad (5)$$

and the corresponding medical condition for the target site is the medical condition for the reference data point(s) x(q0) satisfying Eq. (1), denoted herein as MC(x(q0)). In the one-dimensional illustration in FIG. 8B, the overall probability would be determined by $$PR[y] = F(d(x(B1); y) \quad (y \leq {}^xB1, M1) \quad (6)$$
$$= F(d(x(M1); y) \quad ({}^xB1, M1 < y < {}^xM1, B2)$$
$$= F(d(x(B2); y) \quad (y \geq {}^xM1, B2),$$

where $x_{B1,M1}$ is the value of y at which $F(d(x(B1);y)$ and $F(d(x(M1);y)$ are equal and $x_{M1,B2}$ is the value of y at which $F(d(x(M1);y)$ and $F(d(x(B2);y)$ are equal.

If, for a given observed data point y, J reference data points x(q0j) (j=1, ..., L) are found that satisfy Eq. (1), with J≥1, a modified overall probability Pr[y]/J is assigned to each of the medical conditions associated with the data points x(q0j). Where all J medical conditions are the same, that medical condition is assigned an overall probability of Pr[y] for the target site. Where two (or more) different medical conditions occur, denoted as MC(x(q0j1)) and MC(x(q0j2)) for definiteness, corresponding to different reference data points that each satisfy Eq. (1), a modified overall probability assigns a portion of the probability PR[y], defined in Eq. (5) to each of the medical conditions MC(x(q0j1)) and MC(x(q0j2)).

In a second embodiment, given the observed data point y, a first nearest-neighbor reference data point x(q01) and a second nearest-neighbor reference data point x(q02), corresponding to a malignant medical condition and to a normal medical condition, respectively, are identified, with corresponding probability functions as defined in Eq. (3). The probability that the target site is malignant and the probability that the target site is normal are then taken to be $$Pr(y \in M) = F(d(x(q1);y);q1)/(Sum) \quad (7)$$

and $$Pr(y \in B) = F(d(x(q2);y);q2)/(Sum), \quad (8)$$

respectively, with $$Sum = F(d(x(q1);y);q1) + F(d(x(q2);y);q2). \quad (9)$$

The definitions (7), (8) and (9) ensure that the sum of the probabilities for the two independent events $\{y \in M\}$ and $\{y \in B\}$ is non-negative and is no greater than 1.0. The definitions (7), (8) and (9) extend to a situation where more than one reference data point $x(q) \in M$ satisfies Eq. (1) and/or where more than one reference data point $x(q) \in B$ satisfies Eq. (1).

Each of the first and second embodiments extends from dimension R=1 to any higher integer dimension R. Other formulations of the overall probability Pr[y] associated with the observed data point y can also be used here. This analysis can be combined with an RBNN approach to train a network and to assign probabilities to different medical conditions at a target site, based on comparison of observed and reference data points.

Another useful neural net modeling technique is backpropagation, wherein NN input vectors and NN output vectors are analyzed and used to train a network to associate specific input vectors with specific output vectors and to associate NN input vectors in a desired manner. Standard backpropagation uses a gradient descent analysis, using a conjugate gradient, Newton or other suitable approach. The backpropagation method is summarized in *Neural Network Toolbox For Use With Matlab*, The Math Works, Third Version, 1998, pp. 5-1 through 5-56.

FIG. 8 indicates schematically what an RBNN seeks to accomplish. A first sequence of input vectors or points p(i) in N-dimensional space is provided (N=2 in the representation of FIG. 8), a second sequence of input weight vectors or points u(i) is also provided, and differences $\Delta u(i,j) = u(i) - u(j)$ are formed. One object of a, linear RBNN is to identify one or more input vectors that minimize the perpendicular distances $d(p, \Delta u(i,j))$ between the vector p and the vectors $\Delta u(i,j)$, as illustrated in FIG. 8. It is unlikely that a single input vector p can be found that minimizes all the distances $d(p, \Delta u(i,j))$, but one or more vectors p may be identifiable for which the weighted sum $$\varepsilon(p) = \sum_{i,j} b(i, j) d(p, \Delta u(i, j)) \quad (1)$$

is minimized, where b(i,j) is a non-negative weight assigned to the pair of input weight vectors w(i) and w(j). For normalization purposes, one may restrict the input vectors p to a specified subset, such as the set of all vectors p with unit length: $\|p\| = 1$. The relation $$\epsilon(q) = \text{maximum} \quad (2)$$

among all vectors q with unit length has a well defined mathematical solution, but he set of available input vectors p may not include the exact solution vector q for Eq. (2). Thus, one may have to search among the available input vectors for one or more vectors p that comes closest to satisfying Eq. (2). An RBNN is one method for identifying this optimum vector p. Once an optimum vector p is identified, one can determine confidence levels associated with the optimum vector p belonging to a first medical condition set (e.g., cancer at the target site) and with the optimum vector p belonging to a second medical condition set (e.g., a benign or normal condition at the target site).

What is claimed is:

1. A system for estimating a medical condition associated with a target site in an animal body, the system comprising:
   a first database that contains R-dimensional vector values x(q) of reference values of measurements that characterize one or more medical conditions of the target site in the animal body, with q in Q1 or q in Q2, where Q1 and Q2 are mutually exclusive index sets, where each vector value x(q) in the first database is associated with a first set S1 of medical conditions, corresponding to q being a member of Q1, or with a second set S2 of medical conditions, corresponding to q being a member of Q2, where S1 and S2 are mutually exclusive and R is a selected positive integer;

a second database that contains vector values y in a set S3 of one or more measurements made at or adjacent to the target site, where y is a P-dimensional vector and P is a selected positive integer with $P \leq R$; and a computer that is programmed to form a non-negative, real-valued medical condition function of a metric distance between the vector x(q) and one or more of the vector values y, where the medical condition function distinguishes between a first medical condition in which y is more likely associated with the first set S1 and a second medical condition in which y is more likely associated with the second set S2.

2. The system of claim 1, wherein at least one of said sets S1 and S2 corresponds to at least one of a normal medical condition and a benign medical condition.

3. The system of claim 1, wherein at least one of said sets S1 and S2 corresponds to a malignant medical condition.

4. A system for estimating a medical condition associated with a target site in an animal body, the system comprising:
a first database that contains R-dimensional vector values x(q) of reference values of measurements that characterize one or more medical conditions of the target site in the animal body, with q in Q1 or q in Q2, where Q1 and Q2 are mutually exclusive index sets, where each vector value x(q) in the first database is associated with a first set S1 of medical conditions, corresponding to q being a member of Q1, or with a second set S2 of medical conditions, corresponding to q being a member of Q2, where S1 and S2 are mutually exclusive and R is a selected positive integer;

a second database that contains vector values y in a set S3 of one or more measurements made at or adjacent to the target site, where y is a P-dimensional vector and P is a selected positive integer with $P \leq R$; and a computer that is programmed:
to form a non-negative, real-valued metric d(x(q);y;q), depending upon vectors x(q) and y drawn from the first and second databases, respectively, and upon the index q;

to form a medical condition function F(d(x(q);y;q)), depending upon the metric values d(x(q);y;q), where F is a selected non-negative, monotonically decreasing function of the metric value d(x(q);y;q);

to compute the quantities $F1(y) = \max_{w(q)\ in\ S1} F(d(w(q);y;q))$ and $F2(y) = \max_{w(q)\ in\ S2} F(d(w(q);y;q))$;

when F1(y)>F2(y), to interpret the value F1(y)/{F1(y)+F2(y)} as a lower bound on a probability that the measurement value y is associated with the first set S1, and to interpret the value F2(y)/{F1(y)+F2(y)} as an upper bound on a probability that the measurement value y is associated with the first set S2; and when F1(y)<F2(y), to interpret the value F1(y)/{F1(y)+F2(y)} as an upper bound on a probability that the measurement value y is associated with the first set S1, and to interpret the value F2(y)/{F1(y)+F2(y)} as a lower bound on a probability that the measurement value y is associated with the first set S2.

5. The system of claim 4, wherein said computer is further programmed to draw said function F(z) for a non-negative value z from a group of functions consisting of $F(z) = \exp\{-\alpha \cdot z^p\}$, $F(z) = \{\beta + \chi \cdot z^r\}^{-\gamma}$ and $F(z) = \mu - \nu \cdot z^s$, where $\alpha, \beta, \chi, \gamma, \mu, \nu, p, r$ and $s$ are selected non-negative values.

6. The system of claim 4, wherein said metric d(x(q);y;q) depends upon said vectors x(q) and y and depends upon said index q only through said vector x(q).

7. The system of claim 4, wherein, for at least two distinct values q' and q" with corresponding vectors x(q') in said set S1 and x(q") in said set S2, said metric value d(x(q');y;q') differs from said metric value d(x(q");y;q") for at least one measurement vector y.

8. The system of claim 4, wherein each of said functions F(d(x(q);y;q)) is chosen to satisfy $0 \leq \max_{y\ in\ S3} F(d(x(q);y;q)) \leq 1$ for each vector x(q) and said computer is further programmed to interpret said value F(d(x'(q);y;q)) for at least one vector x'(q) in said set S1 as a probability that said measurement vector y belongs to said set S1.

9. The system of claim 4, wherein each of said functions F(d(x(q);y;q)) is chosen to satisfy $0 \leq \max_{y\ in\ S3} F(d(x(q);y;q)) \leq 1$ for each vector x(q) and said computer is further programmed to interpret said value F(d(x'(q);y;q)) for at least one vector x'(q) in said set S2 as a probability that said measurement vector y belongs to said set S2.

10. The system of claim 4, wherein at least one of said sets S1 and S2 corresponds to at least one of a normal medical condition and a benign medical condition.

11. The system of claim 4, wherein said at least one of said sets S1 and S2 corresponds to a malignant medical condition.

12. A method for estimating a medical condition associated with a target site in an animal body, the method comprising:
providing a first database that contains R-dimensional vector values x(q) of reference values of measurements that characterize one or more medical conditions of the target site in the animal body, with q in Q1 or q in Q2, where Q1 and Q2 are mutually exclusive index sets, where each vector value x(q) in the first database is associated with a first set S1 of medical conditions, corresponding to q being a member of Q1, or with a second set S2 of medical conditions, corresponding to q being a member of Q2, where S1 and S2 are mutually exclusive and R is a selected positive integer;

providing a second database that contains vector values y in a set S3 of one or more measurements made at or adjacent to the target site, where y is a P-dimensional vector and P is a selected positive integer with $P \leq R$; and programming providing a computer that is programmed to form a non-negative, real-valued medical condition function of a metric distance between the vector x(q) and one or more of the vector values y, where the medical condition function distinguishes between a first medical condition in which y is more likely in the first set S1 and a second medical condition in which y is more likely in the second set S2.

13. The method of claim 12, further comprising choosing said at least one of said sets S1 and S2 to correspond to at least one of a normal medical condition and a benign medical condition.

14. The method of claim 12, further comprising choosing at least one of said sets S1 and S2 to correspond to a malignant medical condition.

15. A method for estimating a medical condition associated with a target site in an animal body, the method comprising:
providing a first database that contains R-dimensional vector values x(q) of reference values of measurements that characterize one or more medical conditions of the target site in the animal body, with q in Q1 or q in Q2, where Q1 and Q2 are mutually exclusive index sets, where each vector value x(q) in the first database is associated with a first set S1 of medical conditions, corresponding to q being a member of Q1, or with a second set S2 of medical conditions, corresponding to q being a member of Q2, where S1 and S2 are mutually exclusive and R is a selected positive integer;

providing a second database that contains vector values y in a set S3 of one or more measurements made at or adjacent to the target site, where y is a P-dimensional vector and P is a selected positive integer with $P \leq R$; and providing a computer that is programmed:
  to form a non-negative, real-valued metric d(x(q);y;q), depending upon vectors x(q) and y drawn from the first and second databases, respectively, and upon the index q;
  to form a medical condition function F(d(x(q);y;q)), depending upon the metric values d(x(q);y;q), where F is a selected non-negative, monotonically decreasing function of the metric value d(x(q);y;q);
  to compute the quantities F1(y)=$\max_{w(q) \text{ in } S1}$F(d(w(q);y;q)) and F2(y)=$\max_{w(q) \text{ in } S2}$F(d(w(q);y;q));
  when F1(y)>F2(y), to interpret the value F1(y)/{F1(y)+F2(y)} as a lower bound on a probability that the measurement value y is associated with the first set S1, and to interpret the value F2(y)/{F1(y)+F2(y)} as an upper bound on a probability that the measurement value y is associated with the first set S2; and
  when F1(y)<F2(y), to interpret the value F1(y)/{F1(y)+F2(y)} as an upper bound on a probability that the measurement value y is associated with the first set S1, and to interpret the value F2(y)/{F1(y)+F2(y)} as a lower bound on a probability that the measurement value y is associated with the first set S2.

16. The method of claim 15, further comprising programming said computer to draw said function F(z) for $z \geq 0$ from a group of functions consisting of $F(z)=\exp\{-\alpha \cdot z^p\}$, $F(z)=\{\beta+\chi \cdot z^r\}^{-\gamma}$ and $F(z)=\mu-\nu \cdot z^s$, where $\alpha, \beta, \chi, \gamma, \mu, \nu, p, r$ and $s$ are selected non-negative values.

17. The method of claim 15, further comprising programming said metric d(x(q);y;q) to depend upon said vectors x(q) and y and depends upon said index q only through said vector x(q).

18. The method of claim 15, wherein, for at least two distinct values q' and q", with corresponding vectors x(q') in said set S1 and x(q") in said set S2, further comprising programming said metric value d(x(q');y;q') to differ from said metric value d(x(q");y;q") for at least one measurement vector y.

19. The method of claim 15, further comprising programming each of said functions F(d(x(q);y;q)) to satisfy $0 \leq \max_y {}_{\text{in } s3}$F(d(x(q);y;q))$\leq 1$ for each vector x(q) and further comprising programming said computer to interpret said value F(d(x'(q);y;q)) for at least one vector x'(q) in said set S1 as a probability that said measurement vector y belongs to said set S1.

20. The method of claim 15, further comprising programming each of said functions F(d(x(q);y;q)) to satisfy $0 \leq \max_y {}_{\text{in } s3}$F(d(x(q);y;q))$\leq 1$ for each vector x(q) and further comprising programming said computer to interpret said value F(d(x'(q);y;q)) for at least one vector x'(q) in said set S2 as a probability that said measurement vector y belongs to said set S2.

21. The method of claim 15, further comprising programming said computer so that at least one of said sets S1 and S2 corresponds to at least one of a normal medical condition and a benign medical condition.

22. The method of claim 15, further comprising programming said computer so that at least one of said sets S1 and S2 corresponds to a malignant medical condition.

* * * * *